(12) United States Patent
Crespo Veiga et al.

(10) Patent No.: US 9,198,619 B2
(45) Date of Patent: Dec. 1, 2015

(54) METHOD AND SYSTEM FOR ACTIVITY/REST IDENTIFICATION

(75) Inventors: Cristina Crespo Veiga, Portland, OR (US); Pedro Mateo Riobo Aboy, Portland, OR (US); Jose Ramon Fernandez Bernardez, Vigo (ES); Artemio Mojon Ojea, Vigo (ES)

(73) Assignee: Universidade de Vigo, Vigo (ES)

( * ) Notice: Subject to any disclaimer, the term of this patent is extended or adjusted under 35 U.S.C. 154(b) by 182 days.

(21) Appl. No.: 13/176,716

(22) Filed: Jul. 5, 2011

(65) Prior Publication Data

US 2013/0012836 A1 Jan. 10, 2013

(51) Int. Cl.
*A61B 5/00* (2006.01)
*A61B 5/11* (2006.01)

(52) U.S. Cl.
CPC ............. *A61B 5/7221* (2013.01); *A61B 5/1118* (2013.01); *A61B 5/725* (2013.01); *A61B 5/4812* (2013.01); *A61B 5/6824* (2013.01)

(58) Field of Classification Search
CPC .. A61B 5/4812; A61B 5/4815; A61B 5/4818; A61B 5/1118; A61B 5/6824; A61B 5/7221

USPC .......... 600/595, 300, 301, 587, 549
See application file for complete search history.

(56) References Cited

U.S. PATENT DOCUMENTS

| | | | | |
|---|---|---|---|---|
| 5,197,489 A * | 3/1993 | Conlan | ......... | 600/595 |
| 8,335,769 B2 * | 12/2012 | Kesselman | ............ | 707/679 |
| 8,428,965 B2 * | 4/2013 | Mojon Ojea et al. | ........... | 705/2 |
| 8,562,526 B2 * | 10/2013 | Heneghan et al. | ........... | 600/301 |
| 8,900,153 B2 * | 12/2014 | Bagha et al. | ........... | 600/483 |
| 2004/0100376 A1 * | 5/2004 | Lye et al. | ........... | 340/539.12 |
| 2004/0143855 A1 * | 7/2004 | Tononi et al. | ........... | 800/8 |
| 2004/0243659 A1 * | 12/2004 | Nikitin | ........... | 708/819 |
| 2009/0136092 A1 * | 5/2009 | Springer et al. | ........... | 382/107 |
| 2012/0310587 A1 * | 12/2012 | Tu et al. | ........... | 702/141 |

* cited by examiner

*Primary Examiner* — Max Hindenburg
(74) *Attorney, Agent, or Firm* — Aboy & Associates, PC; Mateo Aboy

(57) ABSTRACT

Disclosed embodiments include a method for automatic identification of activity and rest periods based on an actigraphy signal. According to an embodiment, the method comprises (a) applying one or more filters to the actigraphy signal to generate a filtered actigraphy signal, and (b) comparing the filtered actigraphy signal against an adaptive threshold to generate an output signal corresponding to the activity and rest periods. The method can be implemented as part of a medical apparatus or medical system for automatic activity/rest identification from actigraphy signals.

14 Claims, 5 Drawing Sheets

METHOD AND SYSTEM FOR ACTIVITY/REST IDENTIFICATION

TECHNICAL FIELD

The technical field of disclosed embodiments relates to systems, methods, and medical devices. Specifically, it relates to systems, methods, and devices involving actigraphy.

BACKGROUND

Ambulatory blood pressure monitoring (ABPM) has been widely used over casual office blood pressure (BP) readings to improve the diagnosis and treatment of hypertension and to assess cardiovascular risk [1, 2]. ABPM is a fully automated technique in which BP measurements are taken at regular intervals (usually every 15 to 30 minutes) over a 24 or 48 hour period, providing a continuous BP record during the patient's normal daily activities. The use of ABPM has allowed for the observation of a circadian BP pattern. Typically, there is a decrease in systolic and diastolic BP levels during periods of sleep. Subjects who exhibit a nocturnal BP drop of at least 10% are classified as dippers, the ones who do not show this drop are called non-dippers. Recent studies have shown that non-dipper BP patterns are associated with an increased frequency of cardiovascular events, as well as target-organ damage, and cardiovascular morbidity and mortality [3, 4, 5, 6, 7, 8].

The correct assessment of dipper vs. non-dipper requires the ability to accurately identify activity and rest cycles. Traditionally, determination of activity and rest cycles has been performed by assuming or imposing a fixed schedule (for instance, the activity cycle spanning from 7:00 h to 23:00 h, and the rest cycle from 23:00 h to 7:00 h) [9]. This method can prove highly inaccurate due to individual differences in sleep habits. Another method involves the use of a diary where the subjects under study keep a record of their going to sleep and wake up times. In practice, diaries have proven to be cumbersome and unreliable. Several studies have explored the possibility of using actigraphy to perform identification of sleep/wake cycles, which provides an inexpensive and non-obtrusive method to discriminate between sleep and wake periods based on recorded activity levels [10, 11, 12, 13]. The typical actigraphs are wrist-worn devices that use accelerometers to measure and record movement counts at uniform time intervals with low sampling frequencies (e.g. 1 sample per minute). The actigraphy signal can be used to discriminate between sleep and wake cycles, but an automatic method is needed to perform the identification of activity and rest cycles objectively and accurately. In the last 20 years, several methods have been proposed to automatically identify sleep and wake periods from actigraphy [14, 15, 16]. More recent methods use additional signals such as the electrocardiogram and respiration to achieve better performance [17]. Most of these methods have been designed as an alternative to polysomnography for the study of sleep/wake patterns in patients with sleep disorders and other conditions affecting quantity and quality of sleep [18, 19, 20, 21, 22, 23, 24, 25]. As a consequence, they exhibit a high sensitivity to sleep disturbances, and tend to generate multiple wake identifications during main rest periods. This makes them unsuitable for the identification of activity and rest cycles in the context of ABPM and cardiovascular risk assessment, where the objective is not to detect wake events during periods of sleep, but rather to determine the boundaries between the main activity and rest periods. For this reason, short transitions between states during a main activity or rest cycle are considered invalid in this application.

Currently, there are no methods available to perform automatic activity/rest identification from actigraphy with the accuracy required in clinical applications involving cardiovascular risk assessment using ABPM.

SUMMARY

Disclosed embodiments include a method for identification of activity and rest periods based on an actigraphy signal, the method comprising: (a) applying one or more filters to the actigraphy signal to generate a filtered actigraphy signal using a processing hardware element; and (b) comparing the filtered actigraphy signal against an adaptive threshold to generate an output signal corresponding to the activity and rest periods. The method can be implemented as part of a medical apparatus or medical system for automatic activity/rest identification from actigraphy signals.

BRIEF DESCRIPTION OF THE DRAWINGS

Disclosed embodiments are illustrated by way of example, and not by way of limitation, in the figures of the accompanying drawings.

DETAILED DESCRIPTION

A. Overall Method Description

Disclosed embodiments include a method for identification of activity and rest periods based on an actigraphy signal, the method comprising: (a) applying one or more filters to the actigraphy signal to generate a filtered actigraphy signal using a processing hardware element; and (b) comparing the filtered actigraphy signal against an adaptive threshold to generate an output signal corresponding to the activity and rest periods. According to a particular embodiment, and without limitation, the filters include a rank-order filter and said adaptive threshold is a percentile-based function of the expected number of sleep hours of a subject, and the method further comprises implementing a method for data validation based on an empirical probability model containing information about the maximum number of valid consecutive zeroes during activity and rest periods for a given actigrapher and a patient population, applying an adaptive rank-order filter, and applying one or more morphological filters to eliminate invalid activity and rest transitions. The method can be implemented as part of a medical apparatus or medical system for automatic activity/rest identification from actigraphy signals.

Figure 1:
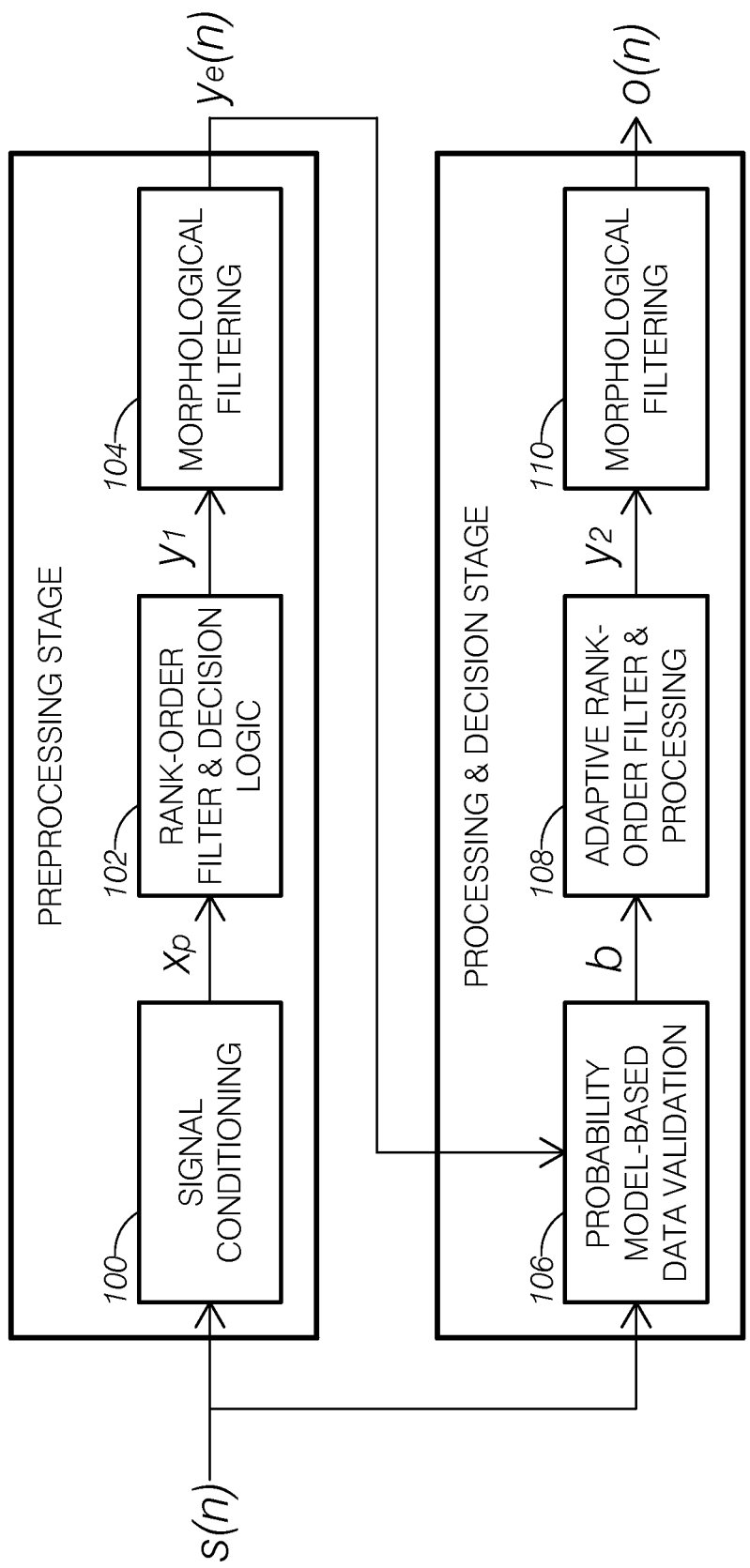
FIG. 1 shows a block diagram of the method for activity/rest identification according to one embodiment.

According to one particular embodiment, as shown in FIG. 1, the method for identification of activity and rest periods is comprised of two stages: 1) a preprocessing stage and 2) a processing and decision stage. The preprocessing stage comprises: a) signal conditioning 100, b) nonlinear filtering and preprocessing decision logic 102, and c) morphological filtering 104 resulting in an initial estimate $y_e(n)$ of the activity/rest periods. This estimate $y_e(n)$, along with the original actigraphy signal $s(n)$, is the input to the processing and decision stage which comprises: a) validating the actigraphy data based on an empirical probability model 106, b) filtering the actigraphy data based on an adaptive rank-order filter 108, and c) postfiltering the result using a morphological filter to eliminate false transitions and generate the final activity/rest identification result $o(n)$ 110.

According to one embodiment, the method further comprises a step in order to measure quality of sleep based on actigraphy by applying one or more methods correlated with a polysomnography signal during detected rest periods. For instance, in order to determine the quality of sleep an actigraphy processing method is applied to the sleep regions detected by the automatic method herein described. According to one embodiment, this is accomplished by using a method substantially equivalent to Sadeh's or Cole's method.

In an alternative embodiment, the method comprises a further processing step to perform nap detection based on processing the actigraphy signal with the aid of the output signal $o(n)$ to determine periods of low activity during the activity periods in order to generate an output signal corresponding to nap periods within the activity periods. This is performed using rank-order filters, morphological filters, and an adaptive threshold based on the expected number of sleep hours during naps. In a particular embodiment, the method also includes a model-based data validation module to differentiate between the nap period and invalid inactivity actigraphy data due to actigraph removals.

According to one embodiment, the method comprises a further processing step for automatically calculating cardiovascular risk parameters based on ABPM and actigraphy, that is, it further comprises calculating one or more ABPM parameters based on the ABPM record and the output signal corresponding to the activity and rest periods in order to determine day (activity) and night (rest) blood pressure (BP) parameters. According to one embodiment, the method blood pressure parameters include awake mean systolic BP, asleep mean systolic BP, awake mean diastolic BP, asleep mean diastolic BP, systolic sleep time relative decline, and diastolic sleep time relative decline.

The following sections describe in detail a particular embodiment, without limitation, of an automatic method for activity/rest identification, as well as the results of an experimental study designed to validate its performance.

B. Detailed Description According to a Particular Embodiment of the Method

The design of an method for the identification of activity/rest cycles presents several challenges. One of such challenges is the identification and processing of invalid zeroes. When working with actigraphy signals, it is common to find sequences of consecutive zeroes (i.e., points where the actigraphy signal has a value of zero). During rest periods, it is more likely to find valid sequences of consecutive zeroes, whereas during the day this likelihood is small, and typically when such sequences appear during activity periods, they correspond to instances where the actigraph has been removed (to take a shower, for instance). The method needs to be capable of automatically identifying the sequences of consecutive zeroes that correspond to invalid data (i.e. actigraph removal), so that they can be processed in a way that they do not affect the output of the method. An empirical probability model was used for this purpose. The details regarding the methods as well as the study performed to generate this model are included in the detail description below. Since the probability of finding valid consecutive zeroes is different for activity and rest periods, a first stage in the method using a combined activity/rest probability model must be able to generate an initial estimate of activity and rest periods so that the two different probability models can be later applied to estimated activity and rest periods separately for a more accurate identification.

FIG. 1 shows a block diagram of the proposed method according to a particular embodiment. The method is comprised of two stages: (1) a Pre-processing stage, and (2) a Processing and Decision stage. The aim of the first stage is to produce an initial estimate of the activity and rest periods from the actigraphy signal. The second stage processes the actigraphy signal using information from this initial estimate to produce a binary signal with the final identification of the activity and rest periods, where rest periods are represented as a 0 and activity periods as a 1. During the first stage, the method processes regions of consecutive zeroes corresponding to invalid data using a combined activity/rest probability model. A rank-order filter is then applied to the signal, and based on an adaptive threshold, a binary signal is generated, where rest periods are represented with a 0, and wake periods with a 1. A morphological filter is finally applied to the binary signal to eliminate invalid transitions. The second stage takes the original actigraphy signal, and using the initial estimate of activity/rest regions from the pre-processing stage, applies separate probability models to estimated activity and rest periods in order to eliminate regions of invalid zeroes. This signal validation and conditioning process is followed by an adaptive rank-order filtering and thresholding operation, which produces a binary signal corresponding to a more refined estimate of activity/rest periods. Finally, a morphological filter is applied to the binary signal to eliminate invalid transitions and obtain the final activity/rest identification signal. Table 1 provides a list of the user-specified input parameters to the method and their default values.

In the following description, we will let $s(n)$ denote the raw actigraphy signal in discrete time and $s=(s_1, s_2, \ldots, s_N)$ denote the corresponding vector of length N, where N represents the number of elements in $s(n)$.

B.1. Stage 1: Preprocessing

The purpose of this stage is to produce an initial estimate of the activity and rest periods from the actigraphy signal.

B.1.1. Signal Conditioning Based on Empirical Probability Model

A function $F\{\cdot\}$ is applied to $s(n)$ in order to determine the regions containing more than $\zeta$ consecutive zeroes, $$a = F\{s(n), \zeta\} \quad (1)$$

where $\zeta$ is determined from an empirical probabilistic model and represents the maximum number of consecutive zeroes considered valid, and $a=(a_1, a_2, \ldots, a_A)$ denotes the indices of $s(n)$ containing the invalid zeroes (i.e. sequences of more than $\zeta$ consecutive zeroes).

The values of $s(n)=(s_1, s_2, \ldots, s_N)$ at index locations $a=(a_1, a_2, \ldots, a_A)$ are replaced by a value $s_t$ corresponding to a user specified percentile t of $s(n)$ which must be chosen to minimize the impact of invalid zeroes. Percentile values above 33% bias the results towards wake classifications and percentiles below 33% towards rest classifications assuming a standard 8 hours of sleep for every 24 hours. The result of this operation is a signal $x(n)$ such that $$x(j) = \begin{cases} s_t & \text{if } j \in a \\ s(j) & \text{if } j \notin a \end{cases} \quad (2)$$

Prior to filtering, x(n) is padded at the beginning and at the end with a sequence of 30·α elements of value m=max{s(n)}. This is done in order to use a filter window of user-specified length $L_w$=(60·α+1) centered about each element of x(n), where α represents the length of the window in hours (8 by default). Since the subject must be awake at the moment when the actigraphy recording is started and stopped the value m used for padding is chosen as the maximum value in the actigraphy signal so that it will bias the beginning and the end of the filtered signal towards an awake state, $$x_p = \left(\underbrace{m, m, \ldots, m}_{30 \cdot \alpha}, x_1, x_2, \ldots, x_N, \underbrace{m, m, \ldots, m}_{30 \cdot \alpha}\right) \quad (3)$$

B.1.2. Rank-Order Processing and Decision Logic

The padded signal $x_p$ is filtered according to the following nonlinear equation to generate the filtered actigraphy time series $x_f(n)$:

$$x_f(n) = M\{x_p(n-30\cdot\alpha), x_p(n-30\cdot\alpha+1), \ldots, x_p(n-1),$$
$$x_p(n), x_p(n-1), \ldots, x_p(n+30\cdot\alpha)\} \quad (4)$$

where M{·} denotes the median operator. Larger values of α result in a lower number of invalid transitions between the rest and awake states at the expense of larger inaccuracies in the determination of the exact transition time. Large α values resulting in window lengths up to 12 hours are possible due to constraints imposed by the following thresholding step, which takes into account the user-specified expected number of rest hours per night (8 hr by default).

A rank-order thresholding operation T{·} is performed on the filtered actigraphy signal to obtain the binary signal $y_1(n)$, where $y_1(n)$=1 for $y_1(n)$>p and 0 otherwise. The threshold p is the percentile of $x_f(n)$ corresponding to $(h_s/24)\cdot 100\%$, where $h_s$ is a user-specified parameter corresponding to the average number of hours of sleep per night (8 by default)

$$y_1(n) = T\{x_f(n)\} \quad (5)$$

B.1.3. Morphological Filtering

The binary signal $y_1(n)$ is further processed using a closing-opening morphological filter of

TABLE 1

Summary of user-specified input parameters for the activity/rest identification method

| Name | Symbol | Default |
|---|---|---|
| Threshold consec. zeroes | ζ | 15 |
| Threshold consec. zeroes (wake) | $\zeta^a$ | 2 |
| Threshold consec. zeroes (rest) | $\zeta^r$ | 30 |
| Percentile for invalid zeroes | t | 33 |
| Median filter window length | $L_w$ | 60.8 + 1 |
| Average hours of sleep per night | $h_s$ | 8 |
| Morph. filter window length | $L_p$ | 60 + 1 | user-specified window length $L_p$ in minutes. The purpose of the morphological filtering is to eliminate invalid transitions such as short periods of rest during activity regions and vice-versa. The result of this operation is the binary signal $y_e(n)$:

$$y_e(n) = (y_1 \bullet L_p) \circ L_p \quad (6)$$

where $y_1 \bullet L_p$ represents the morphological closing operation • on the set $y_1$ by the structuring element $L_p$, that is, $y_1 \bullet L_p = (y_1 \oplus L_p) \ominus L_p$ and $y_1 \circ L_p$ represents the morphological opening operation ∘ on the set $y_1$ by the structuring element $L_p$, that is, $y_1 \circ L_p = (y_1 \ominus L_p) \oplus L_p$, and. The symbols ⊖ and ⊕ represent the morphological erosion and dilation operations, respectively. In the case of a one-dimensional signal the operations of erosion and dilation become the minimum and the maximum operators, respectively.

The output of this first stage is a binary signal $y_e(n)$ containing an initial estimate of the rest (0) and activity (1) periods.

B.2. Stage 2: Processing and Decision Logic

This stage uses information from the previous stage to produce the final identification of the activity and rest periods for the input actigraphy signal.

B.2.1. Model-Based Data Validation

Given the estimated activity and rest periods for the input actigraphy signal, we can apply a function G{·} to the original actigraphy signal s(n) in order to find sequences of more than $\zeta^r$ consecutive zeroes during estimated rest periods, and sequences of more than $\zeta^a$ consecutive zeroes during estimated activity periods, $$b = G\{s(n), \zeta^a, \zeta^r\} \quad (7)$$

where $\zeta^a$ and $\zeta^r$ are determined from empirical probabilistic models and represent the maximum number of consecutive zeroes considered to be valid during estimated activity and rest periods, respectively, and $b = (b_1, b_2, \ldots, b_B)$ represents the indices of s(n) corresponding to invalid zeroes.

B.2.2. Adaptive Rank-Order Processing and Decision Logic

Prior to filtering, s(n) is padded at the beginning and at the end with a sequence of length 60 (i.e. 1 hour) of values m=max{s(n)}. This is done in order to bias the beginning and end of the filtered signal towards an activity identification and avoid multiple invalid transitions close to the edges.

$$x_{sp} = \left(\underbrace{m, m, \ldots, m}_{60}, s_1, s_2, \ldots, s_N, \underbrace{m, m, \ldots, m}_{60}\right) \quad (8)$$

An adaptive median filter $M_a\{\cdot\}$ with a varying window length is next applied to the padded time series. The adaptive median filter outputs the median of the values of s(n) within a moving window whose indices are not contained in b. The maximum filter window length is the user-specified parameter $L_w$. This window is adaptive since invalid zeroes are not included in the median calculation and the length of the window starts as 1 hour at the edges and progressively increases to a maximum window length $L_w$. This is done in order to be able to maintain a symmetric window around the current sample at the points where the distance from the current sample to the end of the padded signal is less than half of the maximum window length. The result of this operation is the filtered signal:

$$x_{fa}(n) = M_a\{x_{sp}(n), b\} \quad (9)$$

The binary output $y_2(n)$ is obtained by a rank-order thresholding operation T{·}, where $y_2(n)$=1 (wake) for $y_2(n)$>p and 0 (rest) otherwise. The threshold p is the percentile of $x_{fa}(n)$ corresponding to $(h_s/24)\cdot 100\%$, where $h_s$ is a user-specified parameter representing the average hours of sleep per night (8 by default):

$$y_2(n) = T\{x_{fa}(n)\} \quad (10)$$

B.2.3. Morphological Filtering

The binary output $y_2(n)$ is further processed using a closing-opening morphological filter in order to eliminate invalid transitions such as short periods of rest in regions of activity and vice-versa. This is the same morphological filtering operation that was applied at the end of the preprocessing stage, but the window length is double in size to the one used then (i.e., $L'_p = 2 \cdot (L_p - 1) + 1$).

$$o(n) = (y_2 \bullet L'_p) \circ L'_p = \{o_1, o_2, \ldots, o_N\} \quad (11)$$

The first and last values of the output binary signal are assigned a binary value of 1 (awake). This heuristic rule is derived from the constraint that the subject must be in an awake state when the actigraph is connected or disconnected.

$$o_1 = o_N = 1 \quad (12)$$

The result of this step is the final discrete binary output signal of length equal to the original actigraphy signal. A binary 0 represents a rest state, and a binary 1 represents an activity state.

B.3. Probability Model Methodology

When working with actigraphy signals, it is common to find regions of consecutive zeroes. Some of these correspond to periods of very low activity (mostly during sleep), and some are the result of momentarily disconnecting the actigraph (to take a shower, for instance). When using actigraphy signals to determine activity/rest cycles, it is necessary to differentiate the regions of consecutive zeroes representing invalid data (i.e., disconnections) from the regions of valid consecutive zeroes (i.e., low activity), in order to avoid misclassifications. A probability model was developed to determine the threshold between the number of consecutive zeroes to be considered valid or invalid. The filter implements this empirical probability model. The methodology outlined below can be used to create empirical probability models for other actigraphs.

Let us assume a situation where we have a perfect database, containing actigraphy signals with true and accurate information regarding what zeroes correspond to low activity and are valid data, and what zeroes are invalid. Let z denote the number of consecutive zeroes. Let $P^j(z)$ denote the probability of finding z consecutive zeroes that are valid in a subject j from a sample under study, that is, $j=1, 2, \ldots, J$, where J represents the number of subjects in the sample under study. For each subject j in the sample under study we can estimate the maximum number of valid consecutive zeroes $\zeta^j$ such that $P^j(z \geq \zeta^j) < 0.05$, that is, $$\zeta^j | \{P^j(z \geq \zeta^j) < 0.05\} \quad (13)$$

where $\zeta^j$ represents the maximum number of consecutive zeroes that are valid for subject j. This estimation can be done using Monte Carlo methods for each subject j (see section B for details), $$\{\zeta^j | \{P^j(z \geq \zeta^j) < 0.05\}\}_{j=1}^{J} = (\zeta^1, \zeta^2, \ldots, \zeta^J) \quad (14)$$

that is, for subject $j=1$, we find that $\zeta^1$ is the maximum number consecutive zeroes that satisfies $P^1(z \geq \zeta^1) < 0.05$ and so on for all the subjects in the sample $j = 1, 2, \ldots, J$.

In the simplest probability model for random data (i.e. the one-sample model) a single unknown probability distribution Z produces the data vector $\zeta = (\zeta^1, \zeta^2, \ldots, \zeta^J)$ by random sampling. The notation $Z \rightarrow \zeta$ indicates the vector $\zeta$ contains an independent and identically distributed sample drawn from Z, $$Z \rightarrow \zeta = (\zeta^1, \zeta^2, \ldots, \zeta^J) \quad (15)$$

The sample $\zeta$ is used to calculate the statistic of interest $\hat{\theta} = s(\zeta)$. To assess the statistical behavior of the statistic $\hat{\theta}$, the bootstrap [26] is employed. In this case, the statistic of interest $\hat{\theta} = s(\zeta)$ is specific percentile $\hat{p}_\zeta$ (i.e. the 90th percentile). Once this statistic of interest $\hat{\theta} = s(\zeta)$ is estimated, the 90% confidence interval is obtained for θ directly using the percentiles of $\hat{\theta}^*$. In order to make use of bootstrap, a probability model for the data is needed. In the case of the one-sample model Z gives the observed data $\zeta = (\zeta^1, \zeta^2, \ldots, \zeta^J)$ by random sampling, $Z \rightarrow \zeta$. To perform bootstrap, the unknown probability distribution Z is substituted for the empirical distribution $\hat{Z}^*$ obtained from the data.

From the empirical distribution $\hat{Z}^*$, it is possible to obtain bootstrap samples by random sampling, $$\hat{Z}^* \rightarrow \zeta^* = (\zeta^{*1}, \zeta^{*2}, \ldots, \zeta^{*J}) \quad (16)$$

These samples enable us to calculate bootstrap replications of the statistic of interest $\hat{\theta}^* = s(\zeta^*)$, from which it is possible to perform probabilistic calculations directly using the bootstrap percentiles, that is, it is possible to use the histogram of $\hat{\theta}^*_k(b)$, $b = 1, 2, \ldots, B$ as an estimate of the probability density function and bootstrap confidence intervals for the population are obtained as, $$\hat{\theta}_{k_{lo}} = 100 \cdot \alpha^{th} \text{ percentile of } \hat{\theta}^*_k\text{'s distribution}$$

$$\hat{\theta}_{k_{up}} = 100 \cdot (1-\alpha)^{th} \text{ percentile of } \hat{\theta}^*_k\text{'s distribution}$$

In the context of this problem, a three sample probability model is used, that is, $F = (Z, Z^a, Z^r)$ where $Z^r$ denotes the probability distribution of the maximum number of valid consecutive zeroes during rest periods, $Z^a$ denotes the probability distribution of the maximum number of valid consecutive zeroes during wake periods, and Z denotes the combined activity/rest probability distribution.

$$Z \rightarrow \zeta = (\zeta^1, \zeta^2, \ldots, \zeta^J) \quad (17)$$

$$Z^a \rightarrow \zeta^a = (\zeta^{a1}, \zeta^{a2}, \ldots, \zeta^{aJ}) \quad (18)$$

$$Z^r \rightarrow \zeta^r = (\zeta^{r1}, \zeta^{r2}, \ldots, \zeta^{rJ}) \quad (19)$$

The procedure described above is used to generate an empirical distribution $F^* = (Z^*, Z^{*a}, Z^{*r})$, calculate the statistic of interest $\hat{\theta} = s(\zeta)$ for each distribution, and assess the statistical behavior of the statistic using bootstrap replicas.

Figure 5:
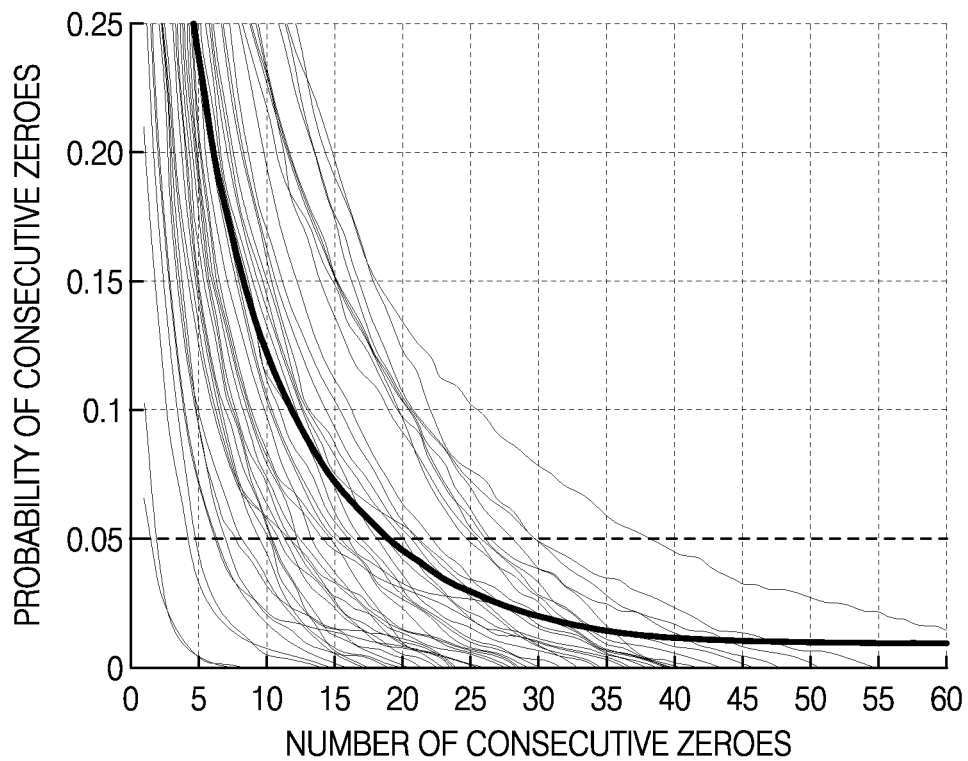
FIG. 5 shows the results of the study to determine the probability of having z consecutive zeroes during activity (top figure) and rest (bottom figure) periods.
Figure 5:
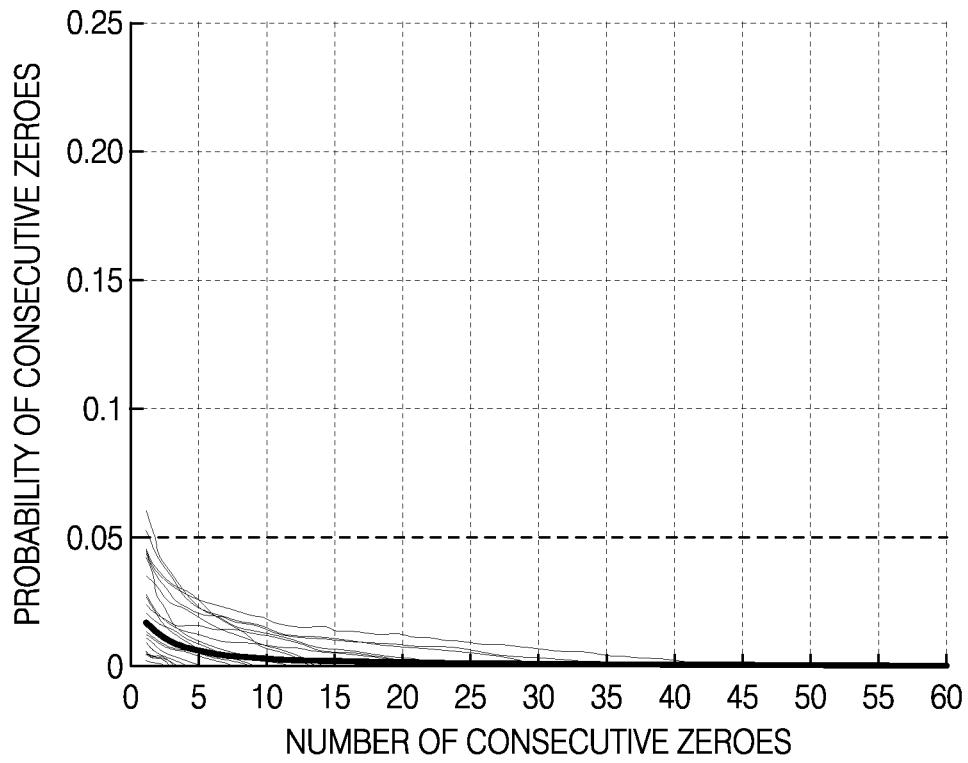

In order to create the empirical probability model for the particular actigraph a study was conducted using a database containing 50 adult healthy subjects, whose actigraphy signals were monitored for 48 hours. The study took place in Galicia (Spain), and it was approved by the state Ethics Committee of Clinical Research. All subjects gave written informed consent. The subjects were diurnally active and nocturnally resting healthy young adult volunteers, 29.51±11.89 years of age. For the duration of the experiment, the subjects were asked to keep an accurate diary of the times when they went to sleep, woke up, and disconnected the actigraph. In practice, diaries are typically imprecise and unreliable. However, in this case the study included research volunteers motivated to keep an accurate diary and the need for accuracy in the diary was strongly emphasized. Using Monte-Carlo methods, a probability model was generated, representing the probability density function for finding a certain number of consecutive zeroes in an actigraphy signal. For every actigraphy signal of length $L = 48 \cdot 60$, $100 \cdot L$ experiments were performed. Each experiment consisted of randomly choosing a sequence of length n from the actigraphy signal, then recording the ratio of the number of sequences selected where all the elements were equal to zero. This was done for values of n such that $1 \leq n \leq L$. FIG. 5 shows the results of the study to determine the probability of having z consecutive zeroes during activity (top figure) and rest (bottom figure)

periods, respectively. The lighter lines represent the probability model for each actigraphy signal, the darker line is an average of these probability models for all the actigraphy signals in the database. Based on the bootstrap analysis of these results, according to one non-limiting embodiment, the method uses $F–(\hat{\zeta}, \hat{\zeta}^a, \hat{\zeta}^r)–(15, 2, 30)$ by default.

C. Experimental Results and Validation of a Particular Embodiment

This section describes the details of a scientific experimental study designed to assess the performance of the proposed method according to one embodiment.

C.1. Assessment Database

The method was validated on a database containing actigraphy recordings of 48 hours for 104 subjects. The study took place in Galicia (Spain), and it was approved by the state Ethics Committee of Clinical Research. All subjects gave written informed consent. The subjects were diurnally active and nocturnally resting healthy young adult volunteers, 22.43±1.66 years of age. All participants wore two actigraphs (Mini-Motion-Logger, Ambulatory Monitoring Inc., Ardsley, N.Y., USA), one on each wrist, to monitor their physical activity every minute. This compact (about half the size of a wristwatch) device functions as an accelerometer. During this experiment, ABPM was also monitored on the non-dominant arm, with ABPM measurements being taken every 20 minutes between 7:00 and 23:00 hours, and every 30 minutes between 23:00 and 7:00 hours. The same computer was always used to synchronize the internal clocks of the two actigraphs. For every subject, the assessment database includes two actigraphy signals, corresponding to simultaneous recordings for the dominant and non-dominant hands, respectively (i.e., 208 recordings). The participants agreed to keep an accurate diary of the times when they went to sleep and woke up for the duration of the experiment. This diary was used as the reference for the assessment and evaluation of the method performance. In practice, diaries are typically imprecise and unreliable. However, in this case the study included research volunteers motivated to keep an accurate diary and the need for accuracy in the diary was strongly emphasized. The average number of sleep hours per night recorded by the subjects included in the validation database ranged from 5 to 11 hours, with 67 out of the 104 subjects recording an average of 8-9 hours of sleep per night.

C.2. Performance Metrics

The assessment of sleep/wake detection methods presented in the literature has been based on metrics that quantify the amount and quality of sleep [14, 15, 16]. These are suitable metrics for the study of sleep disorders and other conditions affecting sleep, but are not relevant or adequate metrics in the context of cardiovascular risk assessment using ABPM. For ABPM applications, the objective is not to assess quantity and quality of sleep, but to accurately identify the boundaries between the main activity and rest periods, so that the value of different ABPM parameters can be calculated separately for activity and rest BP signals. Additionally, ABPM research and clinical practice is based on the underlying idea that it is important to record blood pressure during the normal activity of the subject. Consequently, the gold standard needs to be adequate for collection over 48 hour periods under ambulatory conditions (i.e. during normal daily activity over 2 days). This disqualifies the established gold standard of PSG used in sleep research to assess actigraphy methods, since it is not possible to do acquisition during normal life activities over 48 hours.

For these reasons, a more adequate reference signal was chosen, which could be collected under ambulatory conditions, and a new set of metrics was defined which are more adequate and relevant for the application at hand. The definition of these metrics uses actigraphy signals for both dominant and non-dominant hands, as well as a diary of sleep and wake up times. In order for these metrics to be valid, it is important that the diary be reliable, and therefore the participants in the assessment studies must be motivated and trained to keep an accurate diary. In the absence of a true gold standard, accurate diaries of strongly motivated and trained research volunteers were used as the reference. Diaries have inherent accuracy limitations, and for this reason the carefully collected diary has not been labeled as the "gold standard" but rather the "reference signal." In ABPM applications, where activity and rest have typically been determined by assuming a fixed schedule, the best current practice is to use a diary for determination of main activity and rest cycles, and therefore the selection of reference signal was made so as to match the best current practice.

Three performance metrics (PM) were defined to evaluate the performance of automatic activity/rest identification methods based on actigraphy for ABPM applications. These metrics were labeled PM1 through PM3.

PM1 represents the percent coincidence between the method output and the desired output (diary) in 1-minute intervals.

PM2 represents the percent coincidence between the method output for the dominant versus the non-dominant hand actigraphy signals in 1-minute intervals.

PM3 represents the average number of invalid transitions per 48-hour period.

PM1 provides a measure of the ability of the method to correctly identify 1-minute segments as belonging to an activity or rest period in comparison to the subject's diary. For the application at hand, it is important to have an accurate identification of activity and rest periods, and there is no practical difference between inaccuracies due to false positives or false negatives. For this reason, both types of errors were lumped into a single metric PM1, as opposed to separately measuring specificity and sensitivity. Even though in this experiment it was emphasized that subjects keep an accurate diary of their going to sleep and getting up times, there can be more or less of a delay between the time that a subject records as going to sleep and the time when the subject falls asleep, as well as between the time the subject wakes up and the time later recorded as getting up. PM2 overcomes this limitation by measuring the coincidence between the method output when applied to the dominant versus the non-dominant hand signals. The correlation between the two hands is an indicator of the method's accuracy, since a difference in output between the two hands indicates an incorrect identification for one of the signals (i.e. a subject cannot be in an activity cycle according to one hand, and in a rest cycle at the same time according to the other hand.) PM2 thus provides a measure of the reliability of the result of the method regardless of the value of PM1. Low values of PM2 could indicate that the ABPM monitor is affecting the level of activity in the non-dominant arm, since the placement of the actigraph should have no effect on the performance of activity/rest assessment with actigraphy [27]. This performance metric is independent of the diary, and therefore will not be affected by diary inaccuracies. PM3 is also an important indicator of method performance, as the purpose of the method is to identify main activity and rest periods. This implies we want to avoid short transitions between states, which are sometimes caused by low activity levels during an activity period (e.g., taking a nap during the day) or high activity levels during a rest period (e.g., waking up at night to drink a cup of water). This last metric provides a measure of the robustness of the method to such events. Better method performance corresponds to values for PM1 and PM2 as close as possible to 100%, and values of PM3 as close as possible to zero.

C.3. Validations Results

Figure 2:
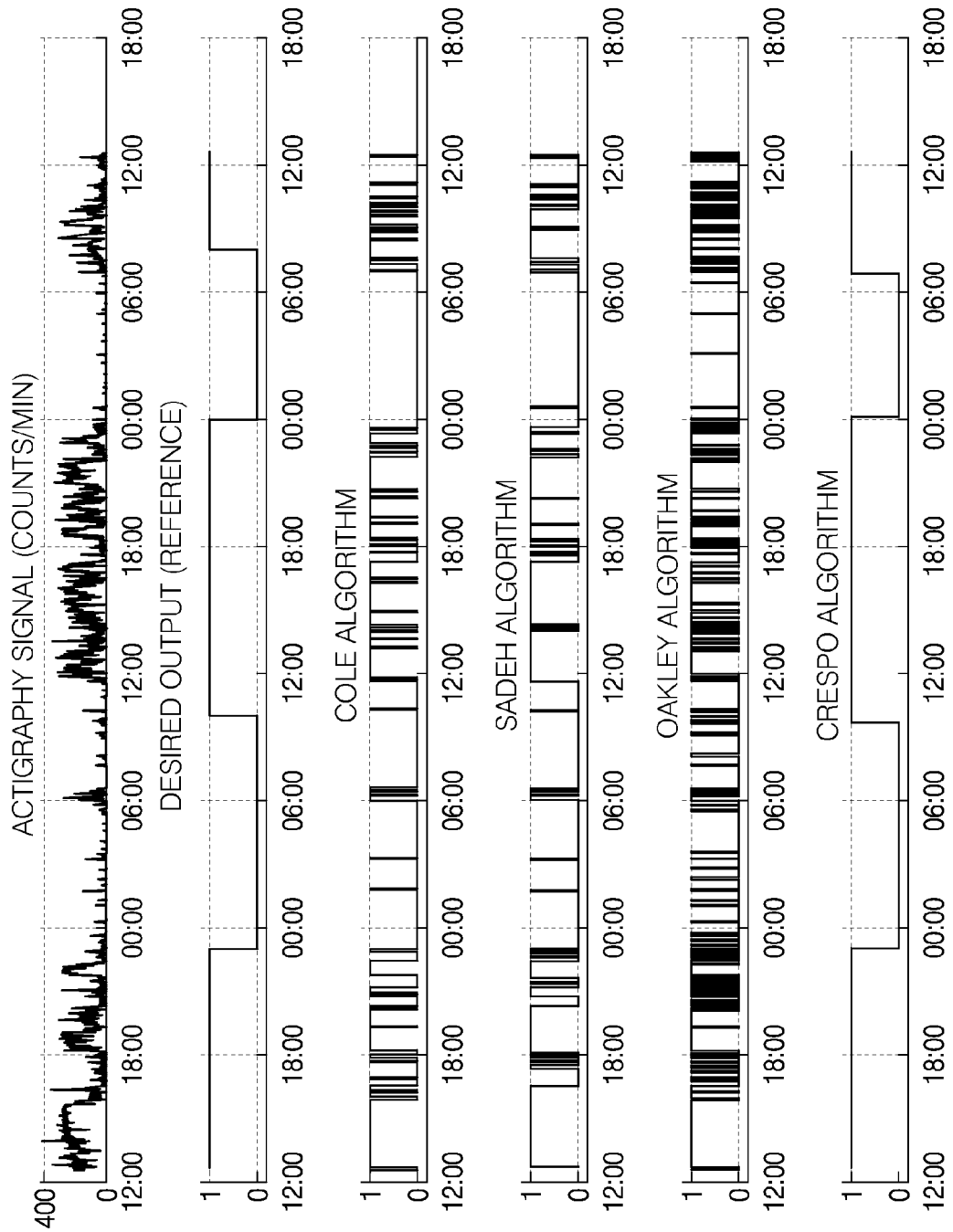
FIG. 2 shows an illustrative example of the input actigraphy signal, the desired output, the results provided by previous methods, and the result provided by an embodiment of the proposed method (Crespo Algorithm).

FIG. 2 provides an illustrative example of the performance of the proposed method as compared to some of the currently available actigraphy methods. The first graph shows an actigraphy signal collected with a wrist actigraph. The second graph corresponds to the activity/rest periods recorded in the diary (i.e., the desired method output). The three plots that follow show the output of some of the classical sleep/wake identification methods (namely, the methods proposed by Cole[15], Sadeh[14], and Oakley[16]). Since these methods have been tailored to the study of sleep disorders, they exhibit a high sensitivity to sleep disturbances, and tend to generate multiple wake identifications during main rest periods. This makes them unsuitable for the identification of activity and rest cycles in the context of ABPM and cardiovascular risk assessment, where the objective is not to detect wake events during periods of sleep, but rather to determine the boundaries between the main activity and rest periods. For this reason, short transitions between states during a main activity or rest cycle are considered invalid in this application. The last plot corresponds to the output of the Crespo method. This example illustrates the advantage of using the proposed method over the classical ones. It can be seen that the Crespo method performs a better identification of the main activity and rest cycles than any of the classical ones, avoiding the large number of invalid transitions detected by these methods.

Figure 3:
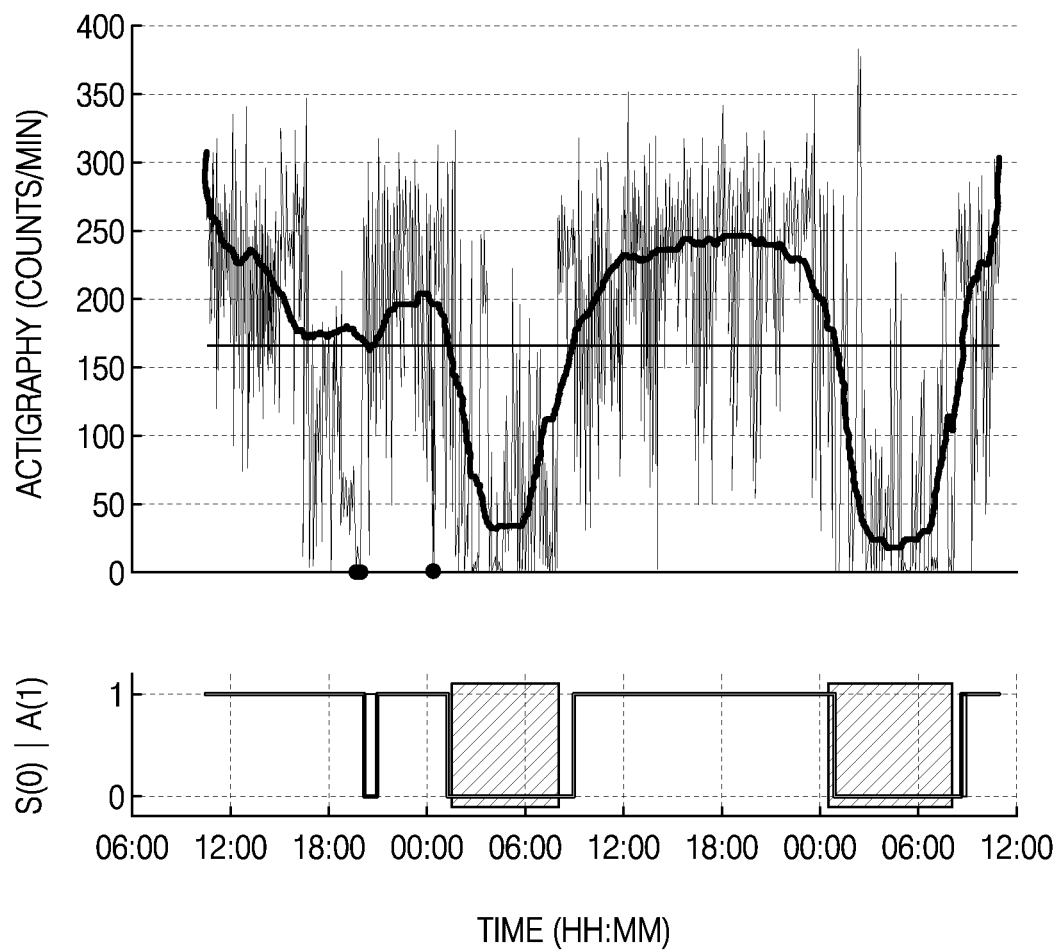
FIG. 3 shows an illustrative example of the proposed method according to one embodiment operating on an input actigraphy signal.

FIG. 3 shows an example illustrating the performance of the proposed method on a real actigraphy signal collected with a wrist actigraph. This figure provides a graphical representation of the different steps performed by the method to produce the binary activity/rest output signal from the original actigraphy signal. On the top graph, a representative actigraphy signal is shown in a light color. During the first stage of the method (i.e., preprocessing stage), the sequences of invalid zeroes are identified and assigned a value equal to the 33% percentile. In the graph, the invalid zeroes appear as a series of dots superimposed on the x-axis. A rank-order filter is then applied to the modified actigraphy signal. The filtered signal is shown in a darker color, superimposed on the raw actigraphy signal. A thresholding operation is performed on the filtered signal, with the threshold set to the appropriate percentile, according to the user-specified average number of sleep hours per night (8 by default). The threshold appears as a light-colored horizontal line at around 165 counts/minute. The initial binary output estimate is generated based on this threshold. Values of the filtered signal lower than the threshold translate into a binary 0 in the output signal, the rest translate into a binary 1.

This initial binary signal is shown in the bottom graph in a lighter color. Finally, a closing-opening morphological filter is applied to the binary signal to eliminate transitions of short duration, which would represent short periods of rest in a wake region, or short periods of activity in a rest region. Since the purpose of the method is to detect the main activity/rest cycle, these short periods are considered invalid. The filtered binary signal appears in a darker color superimposed on the unfiltered binary signal. In this case, an invalid rest period around the 20:00 hours on the first day was corrected by the morphological filter. The two gray boxes on the bottom subplot represent the periods of rest annotated in the diary. A perfect coincidence between the method output and the diary would correspond to an output binary signal which has a value of 0 inside the gray boxes, and a value of 1 everywhere else. FIG. 3 illustrates the robustness of the method when dealing with periods of low activity and disconnections of the actigraph during a wake cycle, such as the period between the 18:00 and 00:00 hours of the first day, due to the ability of the morphological filter to eliminate invalid transitions. In this example, the method performed as follows: PM1 (dominant) was 95.7%, PM1 (non-dominant) was 95.6%, PM2 was 95.7%, and PM3 was 0.

Figure 4:
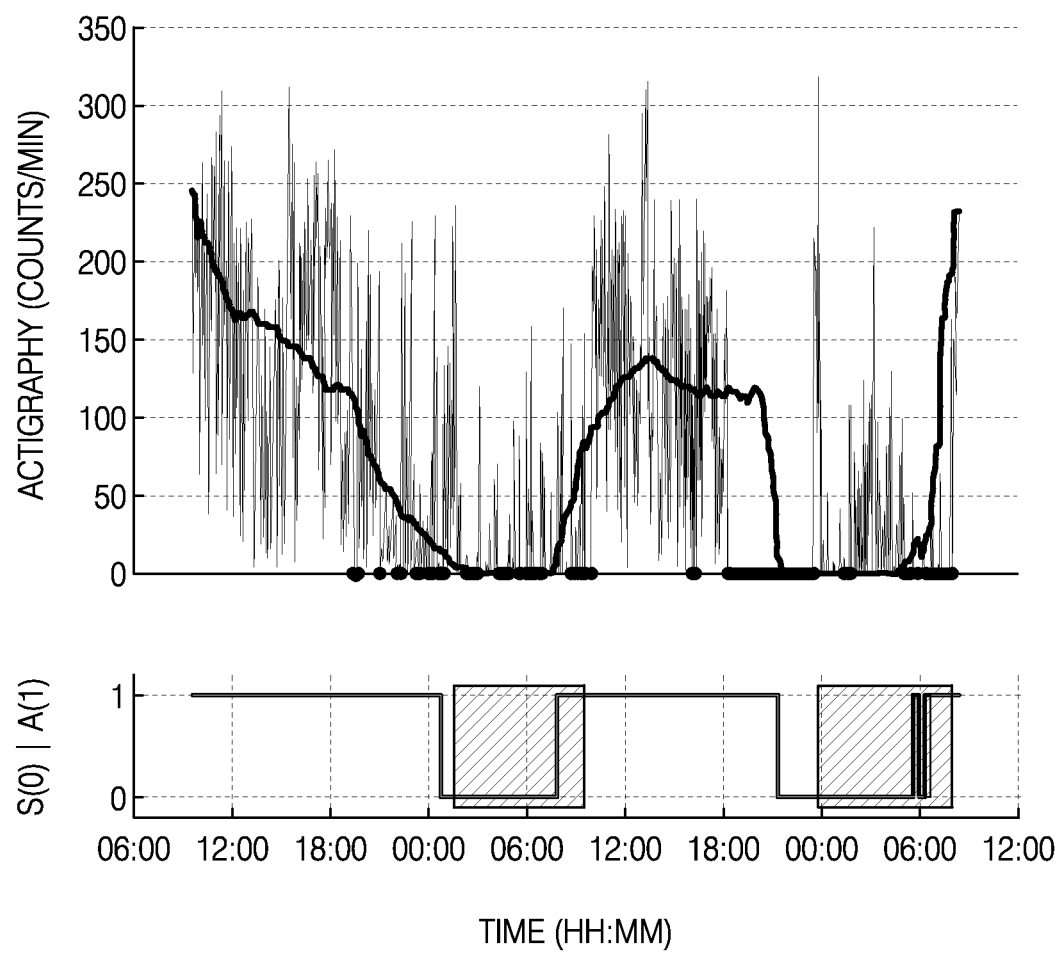
FIG. 4 shows an illustrative example of the proposed method according to one embodiment operating on an input actigraphy signal.

FIG. 4 illustrates the robustness of the method to long periods of invalid data corresponding to unknown disconnection times including disconnections occurring at the transition between wake and sleep periods, as seen between 18:00 and 00:00 of the second day. Additionally, this figure shows the wide range of activity levels during wake periods, as seen in the first day where the transition from the wake to the sleep state occurs progressively and the transition point between the two different states is difficult to identify even by visual inspection.

TABLE 2

This table shows the results of the assessment study for the proposed actigraphy method. The performance metrics shown are the percent coincidence between method and diary using the actigraphy signal from the dominant hand, and the non-dominant hand, respectively, and the percent coincidence between method output for dominant versus non-dominant hands. For each performance metric, the mean and median values are greater than 94.0%, the standard deviation is no greater than 3.3%, and the range of performance (min to max) is better than or equal to 80.6% to 99.1%. In every case, the average number of invalid transitions per 48 hours is 0.02.

|             | PM1 (Dominant) | PM1 (Nondominant) | PM2 (Dom vs Nond) |
|-------------|----------------|-------------------|-------------------|
| Median (%)  | 94.8           | 94.8              | 97.3              |
| Mean (%)    | 94.3           | 94.1              | 96.6              |
| Std Dev (%) | 3.3            | 3.2               | 2.4               |
| Max (%)     | 99.1           | 99.1              | 99.7              |
| Min (%)     | 80.6           | 81.5              | 86.9              |
| Average PM3 | 0.02           | 0.02              | —                 |

The statistical results from the assessment study of the method on the validation database are presented in Table 2. For all the results presented, the user-specified input parameters to the method were set to their default values. This table shows the average statistics of the method performance on the validation database. The performance metrics shown are the percent coincidence between the method output and the diary using the actigraphy signal from the dominant hand, and the non-dominant hand, respectively, and the percent coincidence between the method output for the dominant versus the non-dominant hands. The table shows that the mean value for all three performance metrics is greater than 94.0%, the median is greater than or equal to 97.3% or above, and the standard deviation is no greater than 3.3%. The range of the results over the 104 subjects in the database is between 80.6 and 99.1% when comparing the method output to the diary (using the actigraphy signal from either the dominant or the non-dominant hand), and between 86.9 and 99.7% when measuring the agreement between the output of the method applied to the dominant versus the non-dominant hand. The average number of invalid transitions per 48 hours is 0.02.

D. Medical Apparatus and System

The previous sections described in detail the method for identification of activity and rest periods comprised of two stages: 1) a preprocessing stage and 2) processing and decision stage. As previously described, the preprocessing stage comprises: a) signal conditioning 100, b) nonlinear filtering and preprocessing decision logic 102, and c) morphological filtering 104 resulting in an initial estimate $y_e(n)$ of the activity/rest periods. This estimate $y_e(n)$, along with the original actigraphy signal $s(n)$, is the input to the processing and decision stage, which comprises: a) validating the actigraphy data based on an empirical probability model 106, b) filtering the actigraphy data based on an adaptive rank-order filter 108, and c) postfiltering the result using a morphological filter to eliminate false transitions and generate the final activity/rest identification result $o(n)$ 110. According to one embodiment and without limitation, the method is implemented in an apparatus containing one or more processing elements (e.g. microprocessors, digital signal processors, microcomputers, or any other processing hardware), one or more memories (e.g. RAM, ROM, storage memory, or any other memory device), one or more input hardware elements for controlling and operating said apparatus (e.g. keyboard, mouse, touch screen, or any other input hardware), and one or more output hardware elements for displaying the results of the analysis (e.g. display or any other output hardware including printers). In particular embodiments, such system includes accelerometer data acquisition hardware and software to acquire the actigraphy data required for the method to perform activity/rest identification processing steps. In a particular embodiment, the method is a computer-implemented method that transforms a general purpose computer into a medical apparatus. According to one embodiment, the method is embodied as a set of instructions for causing a hardware device having at least one processor or at least one integrated circuit to perform the method steps of activity/rest identification. In another embodiment, the method is embodied on a storage medium or on a signal for transmission containing the process steps as a set of instructions for causing a hardware device to carry out the method.

According to a specific embodiment, the method can be implemented in a medical system (computer implemented) with one or more processors, physiological signal acquisition systems, analog to digital converters, memory, and output displays such as the typical actigraphs, ambulatory blood pressure monitors (ABPM), or any other medical apparatus. Alternatively, it can be implemented in a digital computer with one or more processors to analyze physiological signals and display or output them.

F. Alternative Embodiments

While particular embodiments have been described, it is understood that, after learning the teachings contained in this disclosure, modifications and generalizations will be apparent to those skilled in the art without departing from the spirit of the disclosed embodiments. It is noted that the embodiments and examples have been provided merely for the purpose of explanation and are in no way to be construed as limiting. While the method/system/apparatus has been described with reference to various embodiments, it is understood that the words which have been used herein are words of description and illustration, rather than words of limitation. Furthermore, although the system has been described herein with reference to particular means, materials and embodiments, the actual embodiments are not intended to be limited to the particulars disclosed herein; rather, the system extends to all functionally equivalent structures, methods and uses, such as are within the scope of the appended claims. Those skilled in the art, having the benefit of the teachings of this specification, may effect numerous modifications thereto and changes may be made without departing from the scope and spirit of the disclosed embodiments in their aspects.

Certain specific details are set forth in the above description and figures to provide a thorough understanding of various embodiments disclosed. Certain well-known details often associated with computing and software technology are not set forth in this disclosure to avoid unnecessarily obscuring the various disclosed embodiments. Furthermore, those of ordinary skill in the relevant art will understand that they can practice other embodiments without one or more of the details described herein. Aspects of the disclosed embodiments may be implemented in the general context of computer-executable instructions, such as program modules, being executed by a computer, computer server, device containing a processor, or specially designed hardware capable of performing computational processing steps. Generally, program modules or protocols include routines, programs, objects, components, data structures, etc. that perform particular tasks, method steps, or implement particular data types. Aspects of the disclosed embodiments may also be practiced in distributed computing environments where tasks are performed by remote processing devices that are linked through a communications network. In a distributed computing environment, program modules may be located in both local and remote storage media including memory storage devices. Those skilled in the art will appreciate that, given the description of the modules comprising the disclosed embodiments provided in this specification, it is a routine matter to provide working systems which will work on a variety of known and commonly available technologies capable of incorporating the features described herein.

REFERENCES

[1] E. Dolan, A. Stanton, L. Thijs, K. Hinedi, N. Atkins, S. McClory, E. D. Hond, P. McCormack, J. A. Staessen, and E. O'Brien, "Superiority of ambulatory over clinic blood pressure measurement in predicting mortality: the dublin outcome study." *Hypertension*, vol. 46, no. 1, pp. 156-161, July 2005. [Online]. Available: http://dx.doi.org/10.1161 /01.HYP.0000170138.56903.7a

[2] L. R. Krakoff, "Ambulatory blood pressure monitoring can improve cost-effective management of hypertension." *Am J Hypertens*, vol. 6, no. 6 Pt 2, pp. 220S-224S, June 1993.

[3] R. C. Hermida, L. Chayán, D. E. Ayala, A. Mojón, M. J. Domínguez, M. J. Fontao, R. Soler, I. Alonso, and J. R. Fernández, "Association of metabolic syndrome and blood pressure nondipping profile in untreated hypertension." *Am J Hypertens*, vol. 22, no. 3, pp. 307-313, March 2009. [Online]. Available: http://dx.doi.org/10.1038/ ajh.2008.358

[4] R. C. Hermida, "Ambulatory blood pressure monitoring in the prediction of cardiovascular events and effects of chronotherapy: rationale and design of the mapec study." *Chronobiol Int*, vol. 24, no. 4, pp. 749-775, 2007. [Online]. Available: http://dx.doi.org/10.1080/ 07420520701535837

[5] C. Cuspidi, S. Meani, M. Salerno, C. Valerio, V. Fusi, B. Severgnini, L. Lonati, F. Magrini, and A. Zanchetti, "Cardiovascular target organ damage in essential hypertensives with or without reproducible nocturnal fall in blood pressure." *J Hypertens*, vol. 22, no. 2, pp. 273-280, February 2004.

[6] C. Cuspidi, I. Michev, S. Meani, B. Severgnini, V. Fusi, C. Corti, M. Salerno, C. Valerio, F. Magrini, and A. Zanchetti, "Reduced nocturnal fall in blood pressure, assessed by two ambulatory blood pressure monitorings and cardiac alterations in early phases of untreated essential hypertension." *J Hum Hypertens*, vol. 17, no. 4, pp. 245-251, April 2003. [Online]. Available: http://dx.doi.org/10.1038/ sj.jhh.1001546

[7] M. Liu, H. Takahashi, Y. Morita, S. Maruyama, M. Mizuno, Y. Yuzawa, M. Watanabe, T. Toriyama, H. Kawahara, and S. Matsuo, "Non-dipping is a potent predictor of cardiovascular mortality and is associated with autonomic dysfunction in haemodialysis patients." *Nephrol Dial Transplant*, vol. 18, no. 3, pp. 563-569, March 2003.

[8] C. Cuspidi, G. Macca, L. Sampieri, V. Fusi, B. Severgnini, I. Michev, M. Salerno, F. Magrini, and A. Zanchetti, "Target organ damage and non-dipping pattern defined by two sessions of ambulatory blood pressure monitoring in recently diagnosed essential hypertensive patients." *J Hypertens*, vol. 19, no. 9, pp. 1539-1545, September 2001.

[9] J. Boggia, Y. Li, L. Thijs, T. W. Hansen, M. Kikuya, K. Björklund-Bodegård, T. Richart, T. Ohkubo, T. Kuznetsova, C. Torp-Pedersen, L. Lind, H. Ibsen, Y. Imai, J. Wang, E. Sandoya, E. O'Brien, J. A. Staessen, and I. D. on Ambulatory blood pressure monitoring in relation to Cardiovascular Outcomes (IDACO) investigators, "Prognostic accuracy of day versus night ambulatory blood pressure: a cohort study." *Lancet*, vol. 370, no. 9594, pp. 1219-1229, October 2007.

[10] S. Ancoli-Israel, R. Cole, C. Alessi, M. Chambers, W. Moorcroft, and C. P. Pollak, "The role of actigraphy in the study of sleep and circadian rhythms." *Sleep*, vol. 26, no. 3, pp. 342-392, May 2003.

[11] L. de Souza, A. A. Benedito-Silva, M. L. N. Pires, D. Poyares, S. Tufik, and H. M. Calil, "Further validation of actigraphy for sleep studies." *Sleep*, vol. 26, no. 1, pp. 81-85, February 2003.

[12] A. Sadeh and C. Acebo, "The role of actigraphy in sleep medicine." *Sleep Med Rev*, vol. 6, no. 2, pp. 113-124, April 2002.

[13] S. W. Lockley, D. J. Skene, and J. Arendt, "Comparison between subjective and actigraphic measurement of sleep and sleep rhythms." *J Sleep Res*, vol. 8, no. 3, pp. 175-183, September 1999.

[14] A. Sadeh, K. M. Sharkey, and M. A. Carskadon, "Activity-based sleep-wake identification: an empirical test of methodological issues." *Sleep*, vol. 17, no. 3, pp. 201-207, April 1994.

[15] R. J. Cole, D. F. Kripke, W. Gruen, D. J. Mullaney, and J. C. Gillin, "Automatic sleep/wake identification from wrist actigraphy," *Sleep*, vol. 15, pp. 461-469, 1992.

[16] L. Tonetti, F. Pasquini, M. Fabbri, M. Belluzzi, and V. Natale, "Comparison of two different actigraphs with polysomnography in healthy young subjects." *Chronobiol Int*, vol. 25, no. 1, pp. 145-153, February 2008. [Online]. Available: http://dx.doi.org/10.1080/07420520801897228

[17] W. Karlen, C. Mattiussi, and D. Floreano, "Improving actigraph sleep/wake classification with cardio-respiratory signals." *Conf Proc IEEE Eng Med Biol Soc*, vol. 2008, pp. 5262-5265, 2008. [Online]. Available: http://dx.doi.org/10.1109/IEMBS.2008.4650401

[18] H. J. Krouse, H. Yarandi, J. McIntosh, C. Cowen, and V. Selim, "Assessing sleep quality and daytime wakefulness in asthma using wrist actigraphy." *J Asthma*, vol. 45, no. 5, pp. 389-395, June 2008. [Online]. Available: http://dx.doi.org/10.1080/02770900801971800

[19] J. Ohinata, N. Suzuki, A. Araki, S. Takahashi, K. Fujieda, and H. Tanaka, "Actigraphic assessment of sleep disorders in children with chronic fatigue syndrome." *Brain Dev*, vol. 30, no. 5, pp. 329-333, May 2008. [Online]. Available: http://dx.doi.org/10.1016/j.braindev.2007.10.004

[20] M. Hyde, D. M. O'Driscoll, S. Binette, C. Galang, S. K. Tan, N. Verginis, M. J. Davey, and R. S. C. Horne, "Validation of actigraphy for determining sleep and wake in children with sleep disordered breathing." *J Sleep Res*, vol. 16, no. 2, pp. 213-216, June 2007. [Online]. Available: http://dx.doi.org/10.1111/j.1365-2869.2007.00588.x

[21] T. Morgenthaler, C. Alessi, L. Friedman, J. Owens, V. Kapur, B. Boehlecke, T. Brown, A. Chesson, J. Coleman, T. Lee-Chiong, J. Pancer, T. J. Swick, S. of Practice Committee, and A. A. of Sleep Medicine, "Practice parameters for the use of actigraphy in the assessment of sleep and sleep disorders: an update for 2007." *Sleep*, vol. 30, no. 4, pp. 519-529, April 2007.

[22] S. H. Jones, D. J. Hare, and K. Evershed, "Actigraphic assessment of circadian activity and sleep patterns in bipolar disorder." *Bipolar Disord*, vol. 7, no. 2, pp. 176-186, April 2005. [Online]. Available: http://dx.doi.org/10.1111/j.1399-5618.2005.00187.x

[23] A. Vallieres and C. M. Morin, "Actigraphy in the assessment of insomnia." *Sleep*, vol. 26, no. 7, pp. 902-906, November 2003.

[24] M. L. Blood, R. L. Sack, D. C. Percy, and J. C. Pen, "A comparison of sleep detection by wrist actigraphy, behavioral response, and polysomnography." *Sleep*, vol. 20, no. 6, pp. 388-395, June 1997.

[25] A. Sadeh, P. J. Hauri, D. F. Kripke, and P. Lavie, "The role of actigraphy in the evaluation of sleep disorders." *Sleep*, vol. 18, no. 4, pp. 288-302, May 1995.

[26] B. Efron and R. Tibshirani, *An Introduction to the Bootstrap*. Chapman and Hall/CRC, 1993.

[27] J. J. V. Hilten, H. A. Middelkoop, S. I. Kuiper, C. G. Kramer, and R. A. Roos, "Where to record motor activity: an evaluation of commonly used sites of placement for activity monitors." *Electroencephalogr Clin Neurophysiol*, vol. 89, no. 5, pp. 359-362, October 1993.

The invention claimed is:

1. A method for identification of activity and rest periods based on an actigraphy signal, said method comprising:
   (a) applying one or more filters to said actigraphy signal to generate a filtered actigraphy signal using a processing hardware element; and
   (b) comparing said filtered actigraphy signal against an adaptive threshold based on the expected number of sleep hours implemented using a percentile of said actigraphy signal to generate an output signal corresponding to said activity and rest periods.

2. The method of claim 1, wherein said one or more filters include at least one nonlinear filter.

3. The method of claim 2, wherein said nonlinear filter is a rank-order filter.

4. The method of claim 3, wherein said adaptive threshold is an user specified function of the expected number of sleep hours of a subject.

5. The method of claim 1, further comprising implementing a method for data validation.

6. The method of claim 5, wherein said method for data validation is based on an empirical probability model, said empirical probability model containing information about a maximum number of valid consecutive zeroes considered during activity and rest periods for a given actigrapher.

7. The method of claim 6, further comprising applying an adaptive rank-order processing and decision logic stage.

8. The method of claim 7, further comprising applying one or more morphological filters to eliminate invalid activity and rest transitions during a preprocessing stage.

9. The method of claim 8, further comprising applying one or more morphological filters to eliminate invalid activity and rest transitions during a processing and decision stage.

10. A medical system for identification of activity and rest periods based on an actigraphy signal, said medical system comprising a processor configured to perform the processing steps of:
(a) applying one or more filters to said actigraphy signal to generate a filtered actigraphy signal; and
(b) comparing said filtered actigraphy signal against an adaptive threshold based on the expected number of sleep hours implemented using a percentile of said actigraphy signal to generate an output signal corresponding to said activity and rest periods.

11. The medical system of claim 10, wherein said one or more filters include a rank-order filter and said adaptive threshold is an user specified percentile-based function of the expected number of sleep hours of a subject.

12. The medical system of claim 11, wherein said processor is further configured to perform the processing steps of a) implementing a method for data validation based on an empirical probability model containing information about the maximum number of valid consecutive zeroes during activity and rest periods for a given actigrapher and a patient population, b) applying an adaptive rank-order filter, and c) applying one or more morphological filters to eliminate invalid activity and rest transitions.

13. An apparatus for identification of activity and rest periods, comprising:
(a) a sensor configured for acquiring actigraphy signals; and
(b) a processor configured for pocking said actigraphy signals by 1) applying one or more filters to said actigraphy signal to generate a filtered actigraphy signal, and 2) comparing said filtered actigraphy signal against an adaptive threshold based on the expected number of sleep hours implemented using a percentile of said actigraphy signal corresponding to $(h_s/24) \times 100\%$ where $h_s$ is a user-specified parameter corresponding to an average number of sleep hours per night to generate and report an output signal corresponding to said activity and rest periods, wherein said one or more filters comprise a median rank-order filter with user-specified window lengths up to 12 hours and a closing-opening morphological filter configured to eliminate invalid sleep-awake and awake-sleep transitions, and padding said actigraphy signal prior to said applying one or more filters at its beginning and end using the maximum value of said actigraphy signal in order to bias its beginning and end towards an awake state.

14. The apparatus for identification of activity and rest periods of claim 13, wherein said processor is further configured to perform the processing steps of a) implementing a method for data validation based on an empirical probability model containing information about the maximum number of valid consecutive zeroes during activity and rest periods for a given actigrapher and a patient population, b) applying an adaptive rank-order filter, and c) applying a second morphological filter to eliminate invalid activity and rest transitions.

* * * * *